(12) United States Patent
Guidi et al.

(10) Patent No.: US 8,835,655 B2
(45) Date of Patent: Sep. 16, 2014

(54) PROCESS FOR PREPARING OLOPATADINE AND/OR A PHARMACEUTICALLY ACCEPTABLE SALT THEREOF

(75) Inventors: Alberto Guidi, Lonigo (IT); Filippo Chiarello, Zermeghedo (IT); Gianmauro Orru', Lonigo (IT); Massimo Verzini, Caldiero (IT); Livius Cotarca, Cervignano del Friuli (IT); Jean-Claude Kizirian, Paris (FR); Elisenda Trepat Guixer, Barcelona (ES); Francisco Marquillas Olondriz, Barcelona (ES)

(73) Assignee: Zach System S.p.A, Bresso (IT)

( * ) Notice: Subject to any disclaimer, the term of this patent is extended or adjusted under 35 U.S.C. 154(b) by 377 days.

(21) Appl. No.: 13/147,741

(22) PCT Filed: Feb. 1, 2010

(86) PCT No.: PCT/EP2010/051148
§ 371 (c)(1),
(2), (4) Date: Oct. 4, 2011

(87) PCT Pub. No.: WO2010/089268
PCT Pub. Date: Aug. 12, 2010

(65) Prior Publication Data
US 2012/0016138 A1    Jan. 19, 2012

(30) Foreign Application Priority Data
Feb. 5, 2009  (EP) ..................................... 09152194

(51) Int. Cl.
*C07D 313/12*  (2006.01)
(52) U.S. Cl.
CPC .................................. *C07D 313/12* (2013.01)
USPC ...................................................... 549/358
(58) Field of Classification Search
CPC ........................................................ C07D 313/12
USPC ......................................................... 549/358
See application file for complete search history.

(56) References Cited

U.S. PATENT DOCUMENTS

| | | |
|---|---|---|
| 4,282,365 A | 8/1981 | Rokach et al. |
| 4,871,865 A | 10/1989 | Lever, Jr. et al. |
| 5,116,863 A | 5/1992 | Oshima et al. |

| | | |
|---|---|---|
| 2005/0288283 A1 | 12/2005 | Hellberg |
| 2007/0232814 A1 | 10/2007 | Bader et al. |
| 2010/0137619 A1 | 6/2010 | Benito Velez et al. |

FOREIGN PATENT DOCUMENTS

| | | |
|---|---|---|
| EP | 0 069 810 | 1/1983 |
| EP | 0 214 779 | 3/1987 |
| EP | 0 235 796 | 9/1987 |
| WO | 2006 010459 | 2/2006 |
| WO | 2007 110761 | 10/2007 |
| WO | 2007 119120 | 10/2007 |

OTHER PUBLICATIONS

Yoshioka et al, Chem. Abs. vol. 89 No. 122903 (1978).*
Ohshima, E. et al., "Synthesis and Antiallergic Activitry of 11-(Aminoalkylidene)-6, 11-Dihydrodibenz[b,e]Oxepin Derivatives", Journal of Medicinal Chemistry, vol. 35, No. 11, pp. 2074-2084, XP-000615220, (May 1, 1992).
"Heterocyclic Compounds", vol. 63, pp. 16365 and 16366, (1965).
International Search Report Issued Aug. 10, 2010 in PCT/EP10/051148 filed Feb. 1, 2010.

* cited by examiner

*Primary Examiner* — Andrew D Kosar
*Assistant Examiner* — Raymond Covington
(74) *Attorney, Agent, or Firm* — Oblon, Spivak, McClelland, Maier & Neustadt, L.L.P.

(57) ABSTRACT

The present invention relates to a process for the preparation of olopatadine and, more particularly, to an improved method of synthesizing olopatadine which comprises reacting a dibenz[b,e]oxepin-11-one derivative of formula (III) and a suitable reagent under Witting condition, and to the intermediate 11-[(Z)-3-(dimethylamino)-propylidene]-6-11-dihydrodibenz[b,e]-oxepin-2-acet-amide p-toluensulfonate salt.

(III)

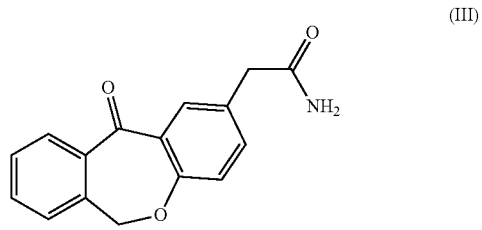

16 Claims, No Drawings

PROCESS FOR PREPARING OLOPATADINE AND/OR A PHARMACEUTICALLY ACCEPTABLE SALT THEREOF

The present invention relates to a process for the preparation of olopatadine and, more particularly, to an improved method of synthesizing olopatadine which comprises reacting a dibenz[b,e]oxepin-11-one derivative of formula

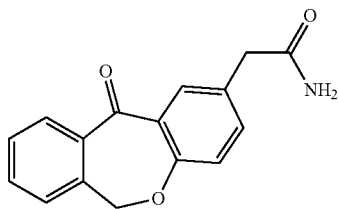

(III)

and a suitable reagent under Witting condition.

Olopatadine, 11-[(Z)-3-(dimethylamino)-propylidene]-6-11-dihydrodibenz-[b,e]-oxepin-2-acetic acid, is a dibenzoxepine derivative of formula

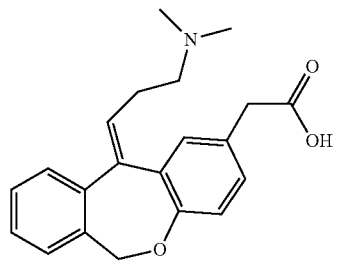

(I)

initially useful for systemic treatment of allergic rhinitis, urticaria and bronchial asthma and developed as a topical anti-allergic agent.

Olopatadine is a relatively selective histamine $H_1$ antagonist and a inhibitor of the release of histamine from mast cells. It is considered to have high affinity for $H_1$ receptor and no effect on alpha-adrenergic, dopaminergic and muscarinic type 1 and 2 receptors.

The hydrochloric acid addition salt is the marketed product which may be administered in a solid oral dosage form or as an ophthalmic solution the latter indicated for the treatment of signs and symptoms of allergic conjunctivitis.

Synthetic approaches to olopatadine generally starts from a common suitably substituted dibenz[b,e]oxepin-11-one substrate. Mainly, two different route are pursued:

Witting reaction with a phosphorus ylide of formula $Ph_3P=CH(CH_2)_2N(CH_3)_2$;

Grignard reaction with a reagent of formula $(CH_3)_2N(CH_2)_3MgX$ followed by dehydration with a strong acid.

Olopatadine base was first described in EP 0214779 (The Wellcome Foundation Ltd.), although no specific examples for its preparation are provided therein. Olopatadine analogues were synthesized, inter alias, by means of the well know Witting method by reaction of a compound of formula

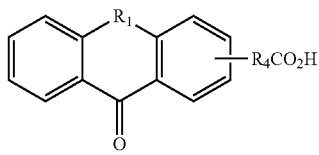

with a Witting reagent $Ph_3P=CH(CH_2)nNR_2R_3$, wherein $R_1$, $R_2$, $R_3$ and $R_4$ have the meaning disclosed in the application which is, in turn, prepared by reacting a compound of formula $Ph_3P-CH_2-(CH_2)nNR_2R_3Br$ with a strong base in a suitable inert solvent. Applicant underlines that protection of the carboxy group may be desirable or required prior to the Witting reaction. Example 5, part b, describes the preparation of 11-[(E/Z)-3-(dimethylamino)-propylidene]-6-11-dihydrodibenz[b,e]-oxepin-2-(E)-acrylic acid by Witting reaction between an ethyl dibenz[b,e]oxepin-11-one acrilate derivative and 3-(dimethylamino)-propyltriphenylphosphonium bromide hydrobromide and subsequent basic deprotection of the ester moiety.

EP 0235796 (Kyowa Hakko Kogyo CO.) describes novel dibenz[b,e]oxepin derivatives useful in the treatment and control of allergic asthma and also in the treatment of inflammation. The application reports several processes for the preparation of olopatadine and analogues thereof. In particular, process C foresees the reaction showed in scheme below

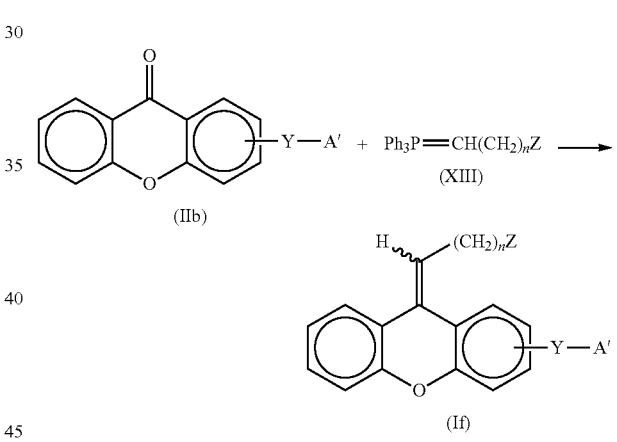

wherein Y, Z, A' and n have the meanings described in the application. Y is, inter alias, $-(CH_2)n$- and A' is, inter alias, carboxy or $-CONR_1R_2$ wherein $R_1$ and $R_2$ are the same or different and represent hydrogen atom or lower alkyl.

Compound XIII which is a phosphorus glide can be prepared according to the method described in C.A. 63, 16366a (1965). Compound (IIb) is reacted with 1-5 equivalents of compound XIII in an inert solvent such as tetrahydrofuran to give If.

The application entails the opportunity to carry out a Witting reaction on a generic protected carboxy group derivative, however, experimental work does not individualize any dimethylaminopropylidene chain insertion on dibenz[b,e]oxepin-11-one amide derivatives.

In the specific olopatadine preparation, Examples 9 and 35, Witting reaction is carried out on an unprotected dibenz[b,e] oxepin-11-one acetic acid derivative. So obtained olopatadine is converted into correspondent ethyl ester and then hydrolysed in order to obtain olopatadine endowed with a suitable E/Z ratio.

Preparation of olopatadine hydrochloride salt, the active ingredient, was first described in J. Med. Chem. 1992, 35, 2074-2084. Dibenz[b,e]oxepin-11-one derivatives possessing a carboxy group connected by an alkyl or vinyl spacer (4c-e) were submitted to Witting reaction and the crude product obtained were esterified for ease of purification. By this method the Z-isomer was preferentially obtained (E/Z=3/7, experimental section E/Z=1/2). So obtained ester is saponified without isomerization and converted into p-toluensulfonate salt which was recrystallized from alcoholic solvent, neutralized, and treated with hydrochloric acid to furnish desired product.

The article reports, in addition, that attempts to prepare the same product under the same Witting condition from corresponding ester protected derivative (e.g. methyl acetate derivative) resulted in the recovery of the starting material.

Literature reports some alternative processes for the preparation of olopatadine. WO 2006/010459 (Urquima S.A.) describes a process for the preparation of olopatadine which comprises the reaction of a compound of formula

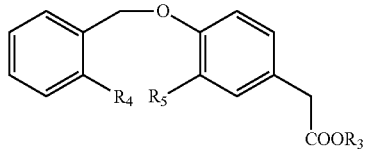

wherein one of $R_4$ and $R_5$ is halogen and the other is CHO and $R_3$ is an acid protecting group; with $Ph_3P(CH_2)_3N(CH_3)_2$ or a salt thereof in the presence of a base. Subsequent palladium catalyzed cyclization and deprotection provide olopatadine.

Acid protecting group means, preferably, an alkyl group, inter alias, methyl is individualized in the experimental work.

WO 2007/119120 (Medichem S.A.) describes new polymorphic forms of olopatadine hydrochloride and methods of preparing, purifying and treating them. Synthetic preparation of olopatadine base comprises classic Witting reaction on 11-oxo-6,11-dihydrodibenzo[b,e]oxepin-2-yl)-acetic acid by using hexyllithium or sodium hydride as strong base.

WO 2007/110761 (Azad Pharmaceutical Ingredient AG) describes a new polymorphic form of olopatadine hydrochloride and method for preparing the same. In particular, the application relates to a method for preparing olopatadine comprising combining 3-dimethylamino propyl triphenylphosphonium halide or a salt thereof, with sodium hydride to provide a reaction mixture which is reacted under Witting condition with 11-oxo-6,11-dihydrodibenzo[b,e]oxepin-2-yl)-acetic acid.

It results apparent from the prior art that Witting reaction plays an essential role in the preparation of olopatadine and, in turn, of the active pharmaceutical acceptable salt.

Nevertheless, prior art methods suffer from significant cost and procedural drawbacks.

In particular, need for excess Witting reagent and strong bases; incomplete dibenz[b,e]oxepin-11-one derivative conversion into the end product in so far as low yields are reported in the literature; poor stereo selectivity in the preparation of Z-pure isomer required; after Witting reaction, protection and deprotection of the carboxylic group increasing the number of reaction steps; moreover, ester derivative purification by chromatography furnishing a Z-enriched derivative which is necessarily further purified by recrystallization.

Hence, it would be desirable to study alternative efficient methods for preparing pure olopatadine or a salt thereof with good yields and under conditions favourable from the industrial application point of view. It would further be desirable to carry out Witting reaction under mild condition, in particular, by reducing the amount of expensive and hazardous reagents and to avoid the need to derivatize olopatadine obtained therefrom.

We have now, surprisingly, found an easy and efficient alternative synthesis of olopatadine amide, key intermediates in preparing olopatadine, which allows to overcome the drawbacks of the processes described in the prior art.

Therefore, a first object of the present invention is a process for preparing a compound of formula

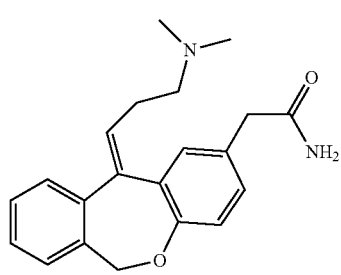

by reacting a compound of formula

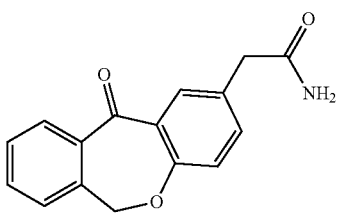

and a 3-dimethylamino propyl triphenylphosphonium halide or a salt thereof in the presence of a base under Witting conditions.

The compound of formula III is prepared in accordance with known methods, for instance, patent EP 0069810 (Merck & CO Inc., US) describes its synthesis starting from correspondent acid derivative.

In one embodiment of the invention, commercially available 11-oxo-6,11-dihydrodibenzo[b,d]oxepin-2-acetic acid is reacted with $SOCl_2$ in toluene to give correspondent chloride which is reacted, in situ, with ammonia to give the compound of formula III as a white powder.

Witting reaction is perfectly known to the skilled person and foresees that an aldehyde or ketone is treated with a phosphorus ylide to give an olefin derivative. Said ylide are generally prepared by treatment of a phosphonium salt with a base.

Thus, Witting conditions entail that phosphonium salt, 3-dimethylamino propyl triphenylphosphonium halide or a salt thereof, is combined with a base to provide a reaction mixture comprising correspondent phosphorous ylide which is reacted with substrate, 11-oxo-6,11-dihydrodibenzo[b,e]oxepin-2-yl)-acetic amide, in a suitable solvent.

Reactant 3-dimethylamino propyl triphenylphosphonium halide or a salt thereof is commercially available and/or may be prepared in accordance with known methods. Patent EP 0235796, process C, furnishes an accurate disclosure of the phosphorous ylide useful in the Witting reaction according to the invention.

Suitable salts are hydrohalide salts and, in particular, hydrobromide, hydroiodine or hydrochloride.

Preferred reactant is 3-dimethylamino propyl triphenylphosphonium bromide hydrobromide.

Suitable bases according to the invention are alkaline hydrides, alkaline alkoxides, alkaline carbonates, organolithium derivatives and the like.

Preferred bases are butyl lithium, hexyl lithium, sodium hydride, potassium hydride, sodium carbonate, potassium carbonate, sodium amide, sodium methoxide, sodium ethoxide, LDA, LiHMDS, KHMDS and the like.

Most preferred base is n-butyl lithium which is, preferably, used in a n-hexane or toluene solution.

Suitable solvents of the invention are ether-type solvent such as tetrahydrofuran and the like, and hydrocarbon, particularly, aromatic hydrocarbon such as toluene and the like.

Preferred solvent is tetrahydrofuran.

Reactant and compound of formula III are used in a molar ratio comprised between 2.0 and 4.0, preferably, they are mixed in a 2.5:1 molar ratio.

Suitable base and compound of formula III are used in a molar ratio comprised between 4.0 and 7.0, preferably, they are mixed in a 5.5:1 molar ratio.

Generally, said reacting a compound of formula III with Witting reagent is carried out at a temperature comprised between −70° C. and 70° C.

The reaction is preferably carried out in the range of −20° C. and 70° C.

Operatively, the reaction mixture coming from combining a strong base with a phosphonium salt is, in situ, reacted with an amide derivative of formula III in an inert solvent to give a compound of formula II endowed with a high purity which is, in turn, further purified and converted into olopatadine or a salt thereof.

Since olopatadine has Z configuration, a compound of formula II is to be further purified in order to increase Z/E ratio, for instance, by conventional methods.

In one embodiment of the invention the aminopropylidene chain is inserted by Witting reaction and obtained amide of formula II (E/Z mixture around 25/75) is purified by crystallization as p-toluensulfonate salt from alcoholic solvent to give highly pure Z-enriched olopatadine amide.

Olopatadine amide from Witting reaction may be recovered as crystal or as solution, preferably as alcoholic solution, and is directly reacted with p-toluensulfonic acid to give correspondent salt which is isolated by filtration.

Said salt may be further purified in accordance with known methods such as recrystallization, preferably, from alcoholic solvent and more preferably from methanol.

Pure olopatadine amide p-toluensulfonate salt is neutralized and hydrolysed to liberate olopatadine free base.

Generally, neutralization and hydrolysis are carried out in the presence of a base or, alternatively, an acid.

Preferred bases are alkaline hydroxide such as sodium or potassium hydroxide.

Preferred acids are mineral acids such as hydrobromic, hydrochloric and sulfuric acid; hydrochloric acid being preferred In a preferred embodiment of the invention olopatadine amide p-toluensulfonate salt is hydrolyzed in the presence of sodium hydroxide.

Pure olopatadine base is then optionally converted into correspondent pharmaceutically acceptable salt in accordance with conventional methods. Olopatadine hydrochloride is the preferred acid addition salt and it may be prepared by reaction with hydrochloric acid in accordance with prior art methods (J. Med. Chem. 1992, 35, 2074-2084).

Therefore, a further object of the present invention is a process for synthesizing olopatadine characterised in that a compound of formula

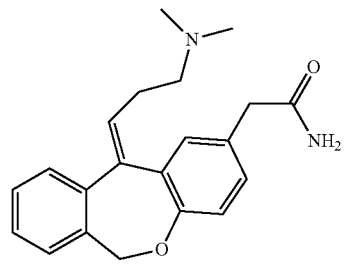

(II)

is prepared by reacting a compound of formula

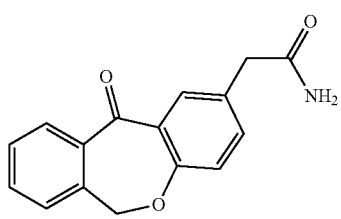

(III)

and a 3-dimethylamino propyl triphenylphosphonium halide or a salt thereof in the presence of a base under Witting conditions.

A further object of the present invention is a process for synthesizing olopatadine which comprises a. reacting a compound of formula

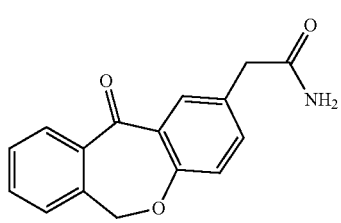

(III)

and a 3-dimethylamino propyl triphenylphosphonium halide or a salt thereof in the presence of a base under Witting conditions, to give a compound of formula

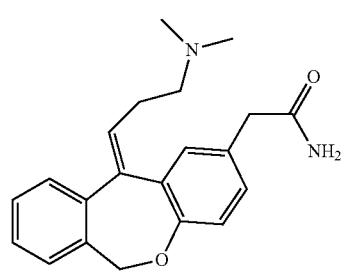

(II)

b. purifying a compound of formula II by fractional crystallization of correspondent p-toluensulfonate salt.

It is a further object of the invention the compound 11-[(Z)-3-(dimethylamino)-propylidene]-6-11-dihydrodibenz[b,e]-oxepin-2-acetamide p-toluensulfonate salt as key intermediate in the preparation of a highly pure olopatadine end product.

A further object of the present invention is a process for synthesizing olopatadine or a pharmaceutically acceptable salt thereof which comprises a. reacting a compound of formula

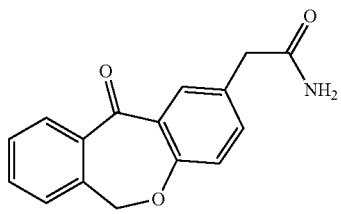

(III)

and a 3-dimethylamino propyl triphenylphosphonium halide or a salt thereof under Witting conditions to give a compound of formula

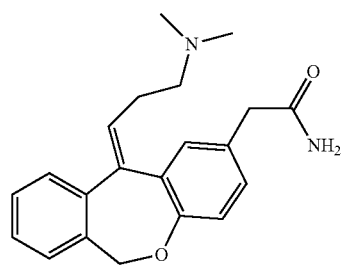

(II)

b. purifying a compound of formula II by fractional crystallization of correspondent p-toluensulfonate salt;

c. hydrolysing so obtained pure Z-isomer of formula II to give olopatadine and optionally converting it into correspondent pharmaceutically acceptable salt.

It is thus evident how the method object of the invention constitutes a suited for industrial production, efficient and economic synthetic alternative for the preparation of olopatadine; in addition, reduced number of synthetic steps and good yields obtained, give notable benefits in terms of process costs and efficiency.

Characterising feature of the invention resides in that Witting reaction is performed on a dibenz[b,e]oxepin-11-one amide derivative.

To the best of inventors' knowledge, the introduction of the dimethylaminopropylidene chain on a primary amide protected acetic moiety under Witting conditions is neither known in the art nor suggested by any prior art reference.

Although prior art entails a generic protection of the acetic moiety, it carries out Witting reaction on an acid substrate; it was confirmed by the inventors that ester derivatives do not withstand Witting conditions and undergo hydrolysis process.

On the contrary, protecting acid moiety as amide derivative allows to reduce the amount of reagents as well as to completely convert starting material into olopatadine amide.

Moreover, Witting reaction performed on an amide substrate according to the invention provides, surprisingly, a product which is highly enriched in the Z-isomer (Z/E=75/25) and, thus, suitable for following purification step aimed to separate the desired Z-pure active ingredient.

For instance, Witting reaction according to the invention by using around 2.5 equivalents of reagent and around 5.5 equivalents of base results in an almost quantitative conversion of a compound of formula III into a diastereoisomeric mixture of olopatadine amide of formula II with a Z/E ratio of around 75/25.

In fact, it appears to be essential to have a Z-enriched derivative in order to simplify purification step which is predominantly carried out by fractional crystallization.

So, the process of the invention does not need for an additional esterification step after Witting reaction as well as purification by column chromatography so as to avoid useless loss in yield.

Subsequent saponification does not undergo isomerization and furnishes a highly pure end product.

A practical embodiment of the process object of the present invention comprises combining a phosphonium salt, 3-dimethylamino propyl triphenylphosphonium halide or a salt thereof, with a base to provide a reaction mixture comprising correspondent phosphorous glide which is reacted with substrate, 11-oxo-6,11-dihydrodibenzo[b,e]oxepin-2-yl)-acetic amide, under Witting conditions.

A preferred practical embodiment of the process object of the present invention comprises converting commercially available 11-oxo-6,11-dihydro-dibenzo-[b,e]-oxepin-2-acetic acid into an amide of formula III; combining 3-dimethylamino propyl triphenylphosphonium halide or a salt thereof, with a base, preferably, butyllithium to provide a reaction mixture which is reacted with said amide of formula III under Witting conditions, preferably, in the presence of an ether type solvent; purifying so obtained amide of formula II (E/Z mixture around 25/75) by crystallization as p-toluensulfonate salt from alcoholic solvent, preferably methanol, to give highly pure Z-enriched olopatadine amide salt; optionally recrystallizing from alcoholic solvent, preferably, from methanol; hydrolysing olopatadine amide p-toluensulfonate salt, preferably in the presence of a base, to liberate olopatadine free base; and converting said free base into correspondent hydrochloride salt.

For better illustrating the invention the following examples are now given.

EXAMPLE 1

Synthesis of 11-oxo-6,11-dihydrodibenzo[b,e]oxepin-2-acetamide

A suspension of 11-oxo-6,11-dihydro-dibenzo-[b,e]-oxepin-2-acetic acid (47 g, 0.1752 mol) in toluene was heated at 90° C. Thionyl chloride (22.9 g, 0.1927 mol) was added and the mixture was stirred for 4 hours at 90° C.

After complete conversion, solvent and excess of reagent was removed by distillation and the residual was diluted with THF, then, added to a 30% wt ammonia solution in water (85.5 ml) at 15° C. Title compound of formula III was isolated by filtration at 0° C. (44.3 g, 95% yield).

EXAMPLE 2

Synthesis of 11-[(Z)-3-(dimethylamino)-propylidene]-6,11-dihydro-dibenzo-[b,e]-oxepin-2-acetamide and Conversion into Correspondent p-toluensulfonate salt To a suspension of 3-dimethylamino propyl triphenylphosphonium bromide hydrobromide (285 g, 0.5615 mol) in THF anhydrous (600 ml) was added at 5° C. a 2.5 M BuLi solution in n-Hexane (491.6 ml, 1.2291 mol) and heated to 25° C. The solution was added to a suspension of a compound of formula III (60 g, 0.2245 mol) in THF anhydrous (600 ml) at 66° C. The mixture was stirred at 66° C. for 4 hours. At reaction completed, the excess of ylide and BuLi was quenched with a 10% wt ammonium chloride solution in water and the organic compounds were extracted in dichloromethane, the waste aqueous layer was discarded. The organic phase was then washed two times with 4N hydrochloride acid and the waste organic layer was discarded. The aqueous layers were collected and pH was adjusted to a value of 13 with a 30% wt sodium hydroxide solution in water and the compound of formula II was extracted with IPAC, concentrated and then diluted with methanol.

Title compound of formula II was so obtained with Z/E ratio around 75/25 in a methanol solution (250 ml, 62.1 g, 83% yield). p-toluensulfonic acid monohydrate (38.5 g, 0.2024 mol) was added to the obtained methanol mixture of a compound of formula II at R.T. and corresponding p-toluensulfonate salt was isolated by filtration at 0° C. and recrystallized from methanol to give pure 11-[(Z)-3-(dimethylamino)-propylidene]-6,11-dihydro-dibenzo-[b,e]-oxepin-2-acetamide p-toluensulfonate salt (50.7 g, 45% yield, Z-isomer>99.5%).

$^1$H-NMR (600 MHz, DMSO-d$_6$): δ=2.25 (s, 3H, $\underline{CH_3}C_6H_5SO_3H$); 2.71 (m, 2H, $CH_2C$=C); 2.73 (s, 6H, $N(CH_3)_2$); 3.24 (m, 2H, $\underline{CH_2}N(CH_3)_2$); 3.30 (s, 2H, $CH_2CONH_2$); 5.16 (m, 2H, $CH_2O$); 5.59 (m, 1H, C=$\underline{CH}CH_2$); 6.75 (dd, J=8.4, 1H, Ar); 6.84 (s, 1H, NH$_2$); 7.04 (m, J=2.1, 1H, Ar); 7.06 (m, J=8.4, 2.1, 1H, Ar); 7.08 (dd, J=8.0, 2H, Ar); 7.25 (dd, J=7.6, 1.2, 1H, Ar); 7.30 (m, J=7.6, 1.2, 1H, Ar); 7.35 (m, J=7.6, 1H, Ar); 7.36 (m, J=7.6, 1.2, 1H, Ar); 7.42 (s, 1H, NH$_2$); 7.45 (dd, J=8.0, 2H, Ar); 9.25 (s, 1H, NH).

$^{13}$C-NMR (20 MHz, DMSO-d$_6$): δ=20.7 ($\underline{CH_3}C_6H_5SO_3H$); 24.8 (CH2=C); 39.4 ($\underline{CH_2}CONH_2$); 42.2 ($N(CH_3)_2$); 55.8 ($\underline{CH_2}N(CH_3)_2$; 69.5 ($CH_2O$); 119.1 (Ar); 122.7 (Ar); 125.4 (Ar); 125.8 (Ar); 126.5 (Ar); 127.8 (Ar); 128.0 (Ar); 128.6 (C=$\underline{CH}CH_2$); 129.0 (Ar); 130.3 (Ar); 131.5 (Ar); 133.5 (Ar); 137.5 (Ar); 141.3 (Ar); 144.4 ($\underline{C}$=CHCH$_2$); 145.7 (Ar); 153.6 (Ar); 172.5 (CONH$_2$).

EXAMPLE 3

Synthesis of 11-[(Z)-3-(dimethylamino)-propylidene]-6-11-dihydro-dibenz-[b,e]-oxepin-2-acetic acid To a suspension in dichloromethane (13.2 ml) methanol (0.6 ml) of p-toluensulfonate salt of a compound of formula II (1.32 g, 0.002595 mol) was added a 5% wt solution of sodium bicarbonate in water (6.6 g, 0.003928 mol). The mixture was stirred 15 minutes and the waste aqueous layer was discarded. The organic layer was washed with a 5% wt solution of sodium bicarbonate in water (4.0 g, 0.002381 mol). The waste aqueous layer was discarded and the organic phase was concentrated, diluted with methanol (6 ml) and a 5M potassium hydroxide solution in water (4.16 ml, 0.0208 mol) was added. The mixture was stirred at 70° C. for 8 hours. At reaction completed, the mixture was cooled to R.T., neutralized to pH 11 with 6N hydrochloride acid. The compound of formula I was purified by absorbing on resin DIAION SK1B (23 ml, 0.0506 mol) and recovered by a 5% ammonia solution in water (511 g) wash. Finally isopropil alcohol (20 ml) was added and the solvent was evaporated to give the title compound (0.388 g, 44.3% yield).

The invention claimed is:

1. A process for preparing a compound of formula

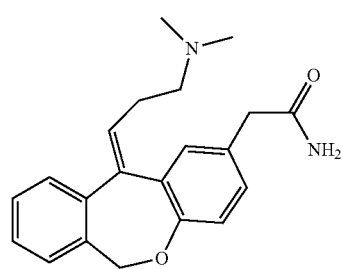

(II)

by reacting a compound of formula

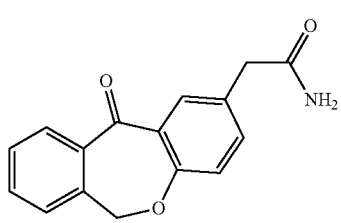

(III)

and a 3-dimethylamino propyl triphenylphosphonium halide or a salt thereof in the presence of a base under Witting conditions.

2. A process according to claim 1 wherein 3-dimethylamino propyl triphenylphosphonium bromide hydrobromide is used.

3. A process according to claim 1 wherein said base is n-butyl lithium.

4. A process according to claim 1 wherein said reacting a compound of formula III and a 3-dimethylamino propyl triphenylphosphonium halide or a salt thereof is carried out in an ether-type solvent.

5. A process according to claim 4 wherein said solvent is tetrahydrofuran.

6. A process according to claim 1 wherein reactant and compound of formula III are used in a molar ratio comprised between 2.0 and 4.0.

7. A process according to claim 6 wherein molar ratio is 2.5:1.

8. A process according to claim 1 wherein base and compound of formula III are used in a molar ratio comprised between 4.0 and 7.0.

9. A process according to claim 8 wherein molar ratio is 5.5:1.

10. A process according to claim 1 wherein said reacting is carried out at a temperature comprised between −20° C. and 70° C.

11. A process for synthesizing olopatadine or a pharmaceutically acceptable salt thereof which comprises a process according to claim 1.

12. A process according to claim 11 further comprising
  a. converting a compound of formula II into correspondent p-toluensulfonate salt;
  b. purifying said salt by fractional crystallization;
  c. neutralizing Z-pure p-toluensulfonate salt;
  d. hydrolysing so obtained Z-pure isomer of formula II to give olopatadine; and e. optionally converting it into a correspondent pharmaceutically acceptable salt.

13. A process according to claim 12 wherein step b is carried out by crystallization from methanol.

14. A process according to claim 12 wherein step d is carried out in the presence of sodium hydroxide.

15. 11-[(Z)-3-(dimethylamino)-propylidene]-6-11-dihydrodibenz[b,e]-oxepin-2-acet-amide p-toluensulfonate salt.

16. A process according to claim 1, wherein the compound of formula (II) is obtained with an E/Z ratio of about 25:75.

* * * * *